US012797639B2

(12) United States Patent
Wulff

(10) Patent No.: US 12,797,639 B2
(45) Date of Patent: Nov. 17, 2026

(54) SPECTRUM MODELING SYSTEMS, METHODS, AND DEVICES FOR PARTICLE THERAPY TREATMENT PLANNING

(71) Applicant: Varian Medical Systems Particle Therapy GMBH & CO.KG, Troisdorf (DE)

(72) Inventor: Joerg Wulff, Krefeld (DE)

(73) Assignee: VARIAN MEDICAL SYSTEMS PARTICLE THERAPY GMBH & CO. KG, Troisdorf (DE)

( * ) Notice: Subject to any disclaimer, the term of this patent is extended or adjusted under 35 U.S.C. 154(b) by 1077 days.

(21) Appl. No.: 17/525,108

(22) Filed: Nov. 12, 2021

(65) Prior Publication Data

US 2022/0072335 A1 Mar. 10, 2022

Related U.S. Application Data

(62) Division of application No. 16/088,101, filed as application No. PCT/EP2017/000376 on Mar. 28, 2017, now Pat. No. 11,235,171.

(60) Provisional application No. 62/315,743, filed on Mar. 31, 2016.

(51) Int. Cl.

| | |
|---|---|
| ***A61N 5/10*** | (2006.01) |
| ***G16H 20/40*** | (2018.01) |
| ***G16H 50/50*** | (2018.01) |
| ***G16H 70/20*** | (2018.01) |

(52) U.S. Cl.

CPC .......... *A61N 5/1031* (2013.01); *G16H 20/40* (2018.01); *G16H 50/50* (2018.01); *G16H 70/20* (2018.01); *A61N 2005/1034* (2013.01); *A61N 2005/1087* (2013.01); *A61N 2005/109* (2013.01)

(58) Field of Classification Search

CPC .... A61N 2005/1034; A61N 2005/1087; A61N 2005/109; A61N 5/1031

See application file for complete search history.

(56) References Cited

U.S. PATENT DOCUMENTS

| | | | | |
|---|---|---|---|---|
| 7,317,192 | B2 * | 1/2008 | Ma | H05H 15/00 250/492.1 |
| 8,632,448 | B1 | 1/2014 | Schulte et al. | |
| 11,235,171 | B2 * | 2/2022 | Wulff | A61N 5/1031 |
| 2014/0005463 | A1 | 1/2014 | Yves | |
| 2015/0202464 | A1 * | 7/2015 | Brand | A61N 5/1031 600/1 |
| 2015/0352374 | A1 | 12/2015 | Gattiker et al. | |

OTHER PUBLICATIONS

Office Action issued Aug. 10, 2020, in Chinese Patent Application No. 201780018393.0.

Supplementary International Search Report and Written Opinion issued Nov. 29, 2018, in European Patent Application No. 17714638.8.

(Continued)

*Primary Examiner* — Christine H Matthews

(74) *Attorney, Agent, or Firm* — Potomac Law Group, PLLC

(57) ABSTRACT

Systems, devices, and methods for non-Gaussian energy distribution modeling for treatment planning algorithms used in particle radiation therapy.

8 Claims, 8 Drawing Sheets

(56) References Cited

OTHER PUBLICATIONS

Tansho et al., "Experimental verification of dose calculation using the simplified Monte Carlo method with an improved initial beam model for a beam-wobbling system," Physics in Medicine and Biology, Institute of Physics Publishing, Bristol GB, vol. 58, No. 17, Aug. 12, 2013, pp. 6047-6064.

International Search Report and Written Opinion dated Jun. 22, 2017, in International Application No. PCT/EP2017/000376.

Office Action issued Feb. 3, 2020, in Chinese Patent Application No. 201780018393.0.

Bellinzona et al., "Implementation of an analytical solution to lateral dose prediction in a proton therapy treatment planning system", Radiotherapy and Oncology, vol. 118, XP029435047, 2016.

Bellinzona et al., "A non Gaussian model for the lateral dose evaluation in hadrontherapy: development and Treatment Planning System implementation", Jan. 1, 2017, pp. 1-114, XP055916866.

Fedotov et al., "IBS for non-gaussian distributions", Sep. 27, 2010, XP055917327.

Office Action issued May 11, 2022, in European Patent Application No. 17714638.8.

* cited by examiner

SPECTRUM MODELING SYSTEMS, METHODS, AND DEVICES FOR PARTICLE THERAPY TREATMENT PLANNING

FIELD

The present disclosure generally relates to particle therapy, and, more particularly, to spectrum modeling for treatment planning algorithms for proton and other charged particle (e.g., neutrons, electrons, heavy ions, etc.) therapy accelerators.

BACKGROUND

Radiosurgery and radiotherapy systems are radiation therapy treatment systems that use external radiation beams to treat pathological anatomies (tumors, lesions, vascular malformations, nerve disorders, etc.) by delivering prescribed doses of radiation (X-rays, gamma rays, electrons, protons, and/or ions) to the pathological anatomy (i.e., the target) while minimizing radiation exposure to the surrounding tissue and critical anatomical structures. Due to the high radiation dose delivered to the patient during the treatment, radiation therapy requires high spatial accuracy to ensure that the tumor or abnormality (i.e., the target) receives the prescribed dose while the surrounding normal tissue is spared.

In general, radiation therapy treatments consist of several phases. First, a precise three-dimensional (3D) map of the anatomical structures in the area of interest (head, body, etc.) is constructed using any one of (or combinations thereof) a computed tomography (CT), cone-beam CBCT, magnetic resonance imaging (MRI), positron emission tomography (PET), 3D rotational angiography (3DRA), or ultrasound techniques. This determines the exact coordinates of the target within the anatomical structure, namely, locates the tumor or abnormality within the body and defines its exact shape and size. Second, a motion path for the radiation beam is computed to deliver a dose distribution that the surgeon finds acceptable, taking into account a variety of medical constraints. During this phase, a team of specialists develop a treatment plan using special computer software to optimally irradiate the tumor and minimize dose to the surrounding normal tissue by designing beams of radiation to converge on the target area from different angles and planes. Third, the radiation treatment plan is executed. During this phase, the radiation dose is delivered to the patient according to the prescribed treatment plan.

Generally, radiation therapy treatment planning is a procedure that takes, as input, a model of both the radiation beam and the patient anatomy, and produces, as output, machine instructions to deliver the radiation treatment (i.e., the beam energy, beam shape and number of photons to be delivered in each beam, etc.), and the expected radiation dose distribution in the patient.

Although treatment planning procedures have some common characteristics for different radiation types, the use of particles (protons, neutrons, heavy ions, etc.) as opposed to photons (i.e., X-rays), has a number of specific implication when it comes to designing and optimizing treatment parameters. The differences come mostly from the fact that particles such as protons deposit most of their energy in a high-dose peak, known as the Bragg peak, at the end of their track, ensuring that the protons stop at the Bragg peak, whereas photons achieve maximum dose either at or just below the surface of the patient and they deposit dose beyond the target.

Generally, in particle therapy, the expected dose distribution within the patient is determined based on dose calculation models that take into consideration the dose at different depths (i.e., depth dose) as well as the distribution of dose in transversal directions (i.e., transversal dose distribution). Since some of the properties of the charged particle beams depend on the initial energy of the beam, the treatment planning for charged particles also models the depth dose distribution of the particles at different energies that are used for the treatment. Therefore, the depth dose distribution usually includes the energy distribution of the particles. Generally, the energy distribution of the particles is approximated by a Gaussian distribution.

It has been observed, however, that for lower energies, the energy distribution of the particles is not necessarily Gaussian. As a result, using a Gaussian distribution to model the energy distribution of the particles to generate the depth dose distribution, may result in a less accurate modeling of the dose distribution. An inaccurate dose distribution model results in inaccuracies in the treatment plan, which can introduce significant differences between the planned and the actual delivered dose.

SUMMARY

Systems and methods are disclosed for modeling energy distribution of one or more particle beams (e.g. charged particle beams) in an object/subject/material using a non-Gaussian distribution.

In exemplary embodiments, the one or more particle beams are one of proton, neutrons, and/or heavy ion beams.

In exemplary embodiments, the object/subject/material is a patient.

In exemplary embodiments, the non-Gaussian model comprises a combination of error functions.

In exemplary embodiments, the non-Gaussian model is given by:

$$p(E) = a\left(Erf\left(\frac{E+b-c}{d}\right) - Erf\left(\frac{E-b-c}{d}\right)\right),$$

where p is the distribution of energy E, a is a normalization constant, b is a width of the profile half, c is the mean energy, and d is a parameter defining the slope of the spectral boundaries.

In other exemplary embodiments, non-Gaussian model is given by:

$$p(E) = a\left(Erf\left(\frac{E+b-c}{d}\right) - Erf\left(\frac{E-b_2-c}{d_2}\right)\right),$$

where p is the distribution of energy E, a is a normalization constant, b and $b_2$ are widths of the profile halves, c is the mean energy, and d and $d_2$ are parameters defining the slope of the spectral higher and lower boundaries.

In exemplary embodiments, depth dose distribution is determined using a non-Gaussian energy distribution model.

In embodiments, radiation dose in an object/subject/material is calculated using a dose calculation algorithm employing a non-Gaussian energy distribution model.

Treatment planning systems, methods, and modules are also disclosed which are configured to determine energy distribution for one or more particle beams, or portions thereof, from a particle therapy system using a non-Gaussian model.

In exemplary embodiments, the determined energy distribution is used to calculate a dose from the one or more particle beams, or portions thereof, within a patient.

In embodiments, the dose calculation can employ an analytical function or a stochastic algorithm.

Particle therapy systems are also disclosed that can comprise: a beam generation system for generating one or more particle beams; a beam transport system for conveying the one or more particle beams from the beam generation system; at least one treatment station for irradiating an object/subject/material with one or more particle beams, the treatment station being coupled to the beam transport system to receive the conveyed one or more particle beams, or portions thereof; a treatment planning module that determines an irradiation plan for the object/subject/material based on energy distribution of particles within said one or more particle beams, or portions thereof; and a controller configured to control at least the beam transport system and the treatment system to effect the irradiation plan.

In exemplary embodiments, the object/subject/material is a patient.

In exemplary embodiments, the treatment planning module is configured to determine the energy distribution based on a non-Gaussian model.

In embodiments, the treatment planning module is configured to use the determined energy distribution to calculate a dose from the one or more particle beams, or portions thereof, within the patient, and the dose calculation can employ an analytical function or a stochastic algorithm.

In embodiments, the non-Gaussian model comprises a combination of error functions.

In embodiments that beam generation system comprises a cyclotron, and the beam transport system can comprise an energy analysis and selection system. The energy analysis and selection system can comprise at least one of a degrader and an energy defining slit.

Methods are also disclosed comprising estimating an energy distribution of particles in one or more particle beams, or portions thereof, from a particle accelerator using a non-Gaussian model.

In exemplary embodiments, the method further comprises irradiating an object/subject/material, such as a patient, for example, with the one or more particle beams, or portions thereof, based at least in part on the determined energy distribution.

In exemplary embodiments, the method can further comprise calculating a dose from the one or more particle beams, or portions thereof, within the patient based on the determined energy distribution. The calculating of the dose may employ an analytical function or a stochastic algorithm.

In exemplary embodiments, the irradiating includes adjusting an energy of the one or more particle beams, or portions thereof, from a particle accelerator using at least one of a degrader and an energy defining slit.

In exemplary embodiments, the non-Gaussian model comprises a combination of error functions.

In exemplary embodiments, the particle beam comprises protons, ions, or other charged particles.

Non-transitory computer readable mediums are also disclosed, comprising instructions for performing any one or a combination of method steps disclosed throughout the written disclosure.

BRIEF DESCRIPTION OF DRAWINGS

Embodiments will hereinafter be described with reference to the accompanying drawings, which have not necessarily been drawn to scale. Where applicable, some features may not be illustrated to assist in the illustration and description of underlying features. Throughout the figures, like reference numerals denote like elements.

DESCRIPTION

High energy particles provide a clinical advantage over other external beam radiation therapy techniques due to their Bragg peak. Due to their depth dose distribution, which allows for maximum dose to be delivered to the tumor volume with no primary particle dose beyond the distal edge, particle therapy techniques allow for the delivery of fewer beams to achieve the same target coverage, in turn limiting the integral dose delivered to other organs and tissues surrounding the targeted site (i.e., target volume, such as a cancerous tumor in a patient, for example).

Particle therapy systems generally include systems and mechanisms to accelerate, transport, and deliver the charged particles to a given target volume within the patient. Typically, the particles are accelerated in an accelerator, such as a cyclotron or synchrotron, and then transported along an evacuated beam pipe to a treatment room. During acceleration and transport, magnets control the direction and focus of the charged particle beam. When the beam arrives at the treatment room, it must be delivered to the target site. This can be achieved using a gantry that allows for beams delivered 360 degrees around the patient.

Figure 1:
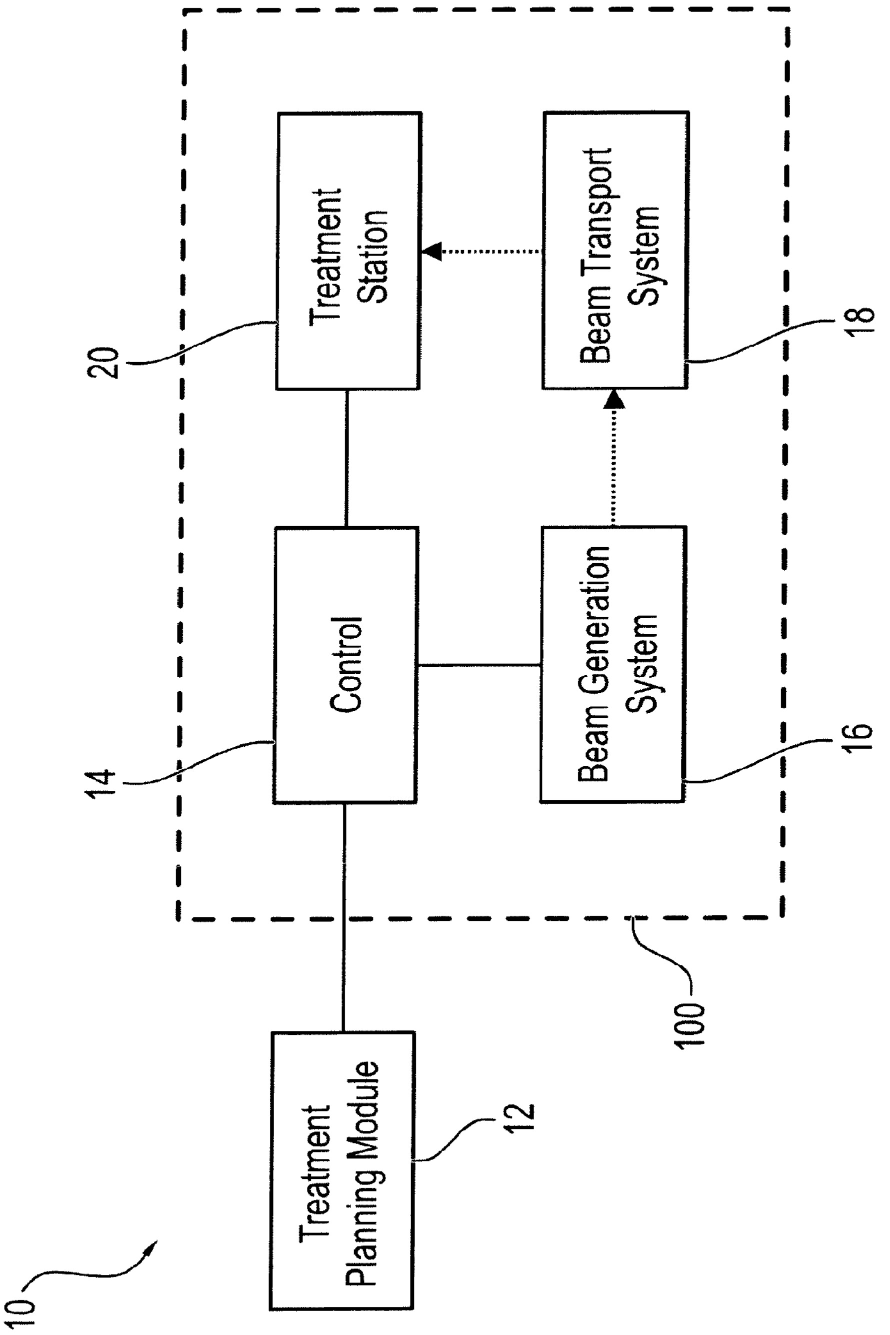
FIG. 1 is a simplified schematic diagram showing the relationship of various components of a treatment system, according to one or more embodiments of the disclosed subject matter.

FIG. 1 shows various components of an exemplary particle therapy system 10. For example, the particle therapy system 10 can include a treatment planning module 12, a controller 14, a beam generation system 16, a beam transport system 18, and a treatment station 20. High energy particles, e.g., protons or other charged particles (e.g., neutrons, electrons, heavy ions, etc.), can be generated by beam generation system 16 and delivered to treatment 20 via beam transport system 18 for irradiation of an object, such as a patient. The beam generation system 16 can include a particle accelerator (e.g., cyclotron or synchrotron), where a particle beam is produced in a specific level of energy that can be adjusted to a prescribed energy level by energy selection. Typically, a particle beam output from the accelerator has a fixed energy. This energy can be anywhere between 70 MeV and 250 MeV. Since the depth of the Bragg peak in a given medium (such as a patient) depends on its initial energy, varying this energy allows the high dose to be placed at any depth within the medium/patient. Energy can be varied/tuned to a desired energy using an energy selection system. Thus, the depth of particle penetration can be varied by varying the energy of the particle beam output from the particle accelerator.

The beam transport system 18 can tune and deliver the particle beam to the treatment station 20 using various magnets for focusing and/or re-directing the particle beam to the treatment station 20. At the end of the beam transport system 18, a rotational gantry associated with an irradiation nozzle delivers the particle beam onto the target volume (e.g., a tumor) of a patient. The irradiation nozzle directs the particle beam at the irradiation object while the patient is positioned on a support mechanism, such as an adjustable gurney or chair configured to hold the patient in a fixed position relative to the particle beam. The rotatable gantry is configured to rotate the irradiation nozzle about the patient to irradiate the desired target volume within the patient from different angles. The adjustable gurney or chair can have six degrees of freedom. The combination of gantry charged beam delivery and the six-degrees of freedom robotic patient gurney/chair allows clinicians great flexibility in particle beam delivery in treating the target volume while sparing critical structures. By varying the energy and by rotating the gantry, both the depth and the position of the particle beam may be varied to treat a three-dimensional volume within a patient.

The treatment planning module 12 determines a treatment plan based on which the target volume within a patient is irradiated in the treatment station 20. The treatment planning module 12 determines the expected radiation dose distribution within the patient based on an inputted model of the particle beam and the patient anatomy. The treatment planning module 12 also outputs machine instructions to be implemented by the beam generation, beam transport, and beam delivery elements of the particle therapy system 10 to ensure proper delivery of the particle beam to achieve the expected dose distribution within the patient. In essence, the treatment planning module 12, determines the energy and position of the particle beams for effective irradiation of the targeted tumor volume, and develops machine instructions to be implemented by the particle therapy system 10 during patient treatment in the treatment station 20 to achieve the expected radiation dose distribution within the patient.

The controller 14 can control one or more of the beam generation system 16, the beam transport system 18, and the gantry to irradiate the patient to effect the desired treatment based on the determined treatment plan from the treatment planning module 12.

In some configurations, the treatment planning module 12 can be provided separate from the other components. For example, the controller 14, beam generation system 16, beam transport system 18 and treatment station 20 may be co-located as an integrated treatment system 100, with the treatment planning module 12 comprising a separate terminal or device. In other configurations, the treatment planning module 12 constitutes a part of the controller 14. In still other configurations, the beam generation system 16 and the beam transport system 18 may be considered separate from the treatment station 20 and/or controller 14, for example, when a single beam generation system 16 and beam transport system 18 are used to supply a particle beam to several different treatment stations 20.

Figure 2:
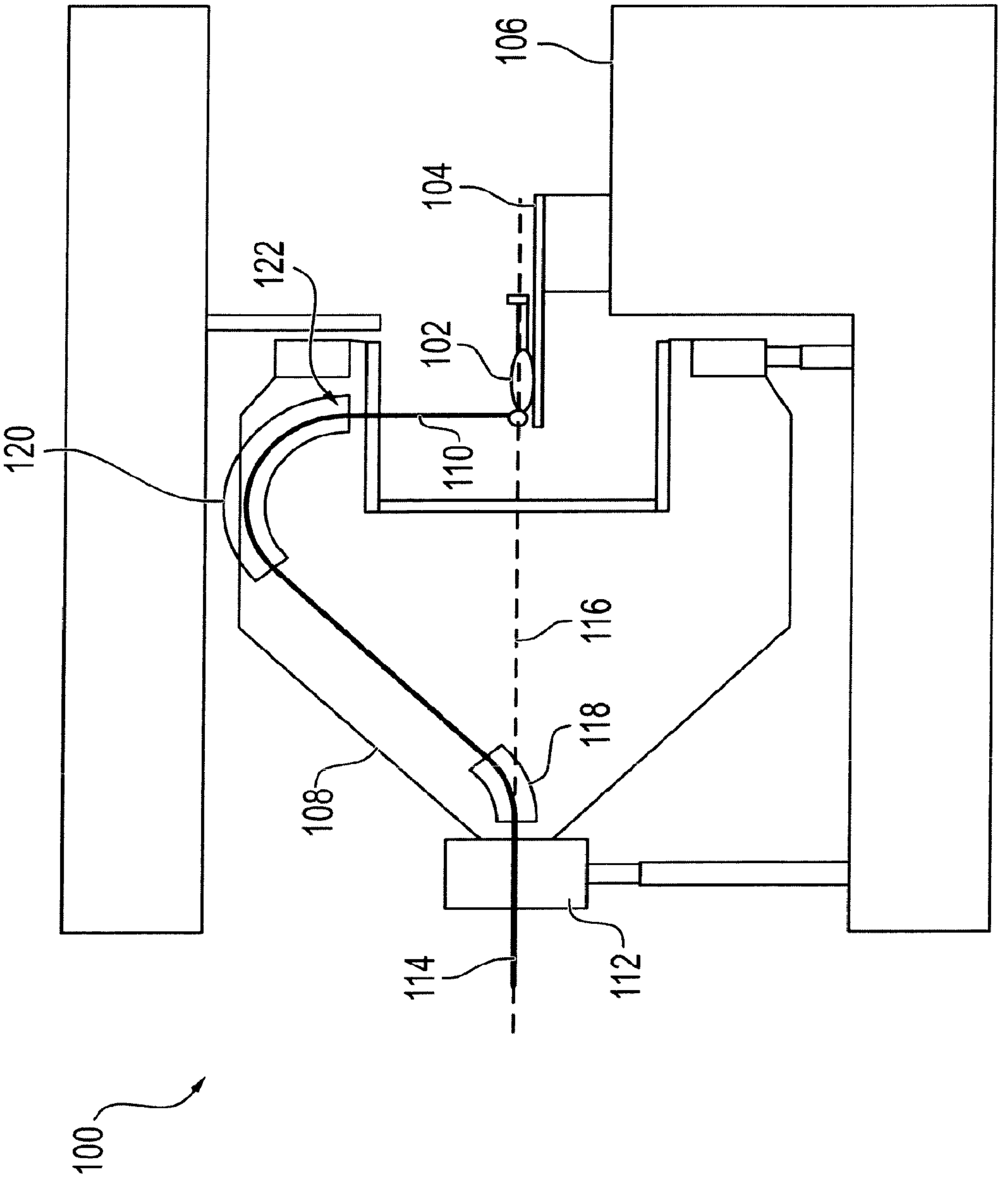
FIG. 2 shows particle irradiation of a patient by the gantry components of a treatment system, according to one or more embodiments of the disclosed subject matter.

A configuration of the treatment station 20 is shown in FIG. 2. The treatment station receives a particle beam 114, for example, a proton beam, from a particle beam source (not shown), such as a cyclotron or synchrotron. The particle beam 114 is transported from the particle beam source via a beam transport system (not shown) that provides the beam 114 to the gantry 108 for irradiating a patient 102. The beam transport system can include a vacuum tube and beam control components, such as, quadrupole magnets that focus the particle beam and dipole magnets that deflect the particle beam.

The particle beam 114 enters the gantry 108 via a rotating vacuum seal 112. Within the gantry 108, the particle beam can follow a serpentine path to an irradiation nozzle 122, which redirects the particle beam along path 110 for irradiation of the patient 102. Magnets 118 and 120 within gantry 108 redirect the particle beam from the vacuum seal 112 to the irradiation nozzle 122. A patient support 104 positions the patient 102 aligned with a rotation axis 116 of the gantry 108. The irradiation nozzle 122 is rotated around the rotation axis 116 by the gantry 108 to irradiate the treatment volume within the patient from different angles.

Configurations and setups for the particle therapy system 10 other than those specifically described above are also possible according to one or more contemplated embodiments. For example, a particle therapy system can have multiple treatment stations 20 (e.g., as separate rooms) that are provided with a particle beam from beam generation system 16 (e.g., a single cyclotron or multiple cyclotrons or synchrotrons) via a common beam transport system 18. In such configurations, the beam transport system 18 can include, for example, a dividing magnet for splitting the particle beam between different treatment stations 20.

Figure 3:
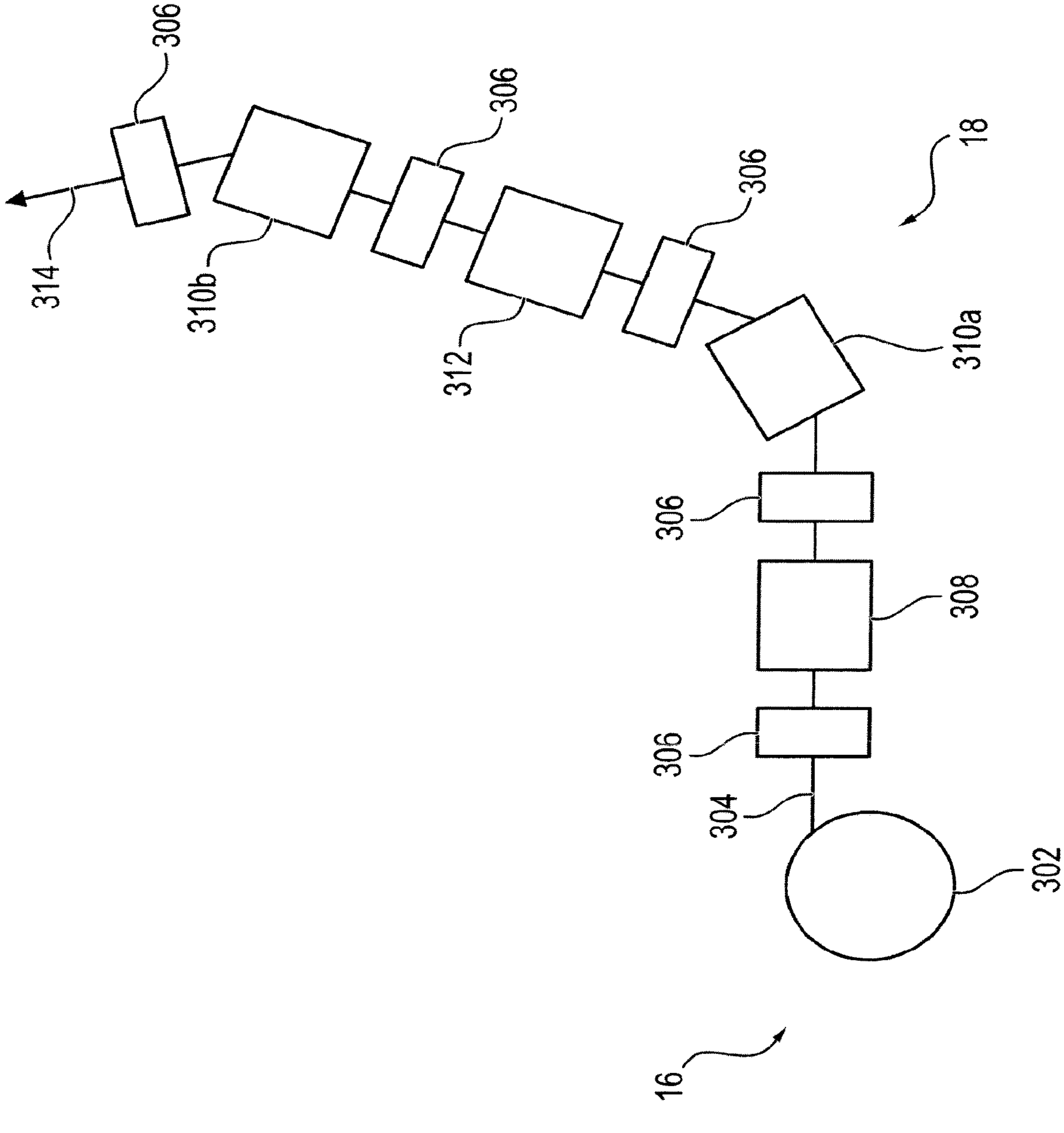
FIG. 3 shows the relationship of various components of particle beam generation and transport in a treatment system, according to one or more embodiments of the disclosed subject matter.

Referring to FIG. 3, an exemplary configuration of portions of beam generation 16 and beam transport system 18 are shown. For example, the beam generation system 16 can include a cyclotron/synchrotron 302 that produces high energy particle beam 304 (e.g., protons or other charged particles, such as ions) for transport by the beam transport system 18. The beam transport system 18 can include one or more magnets 306 for focusing or redirecting the particle beam 304 at various locations along the beam propagation path. Disposed along the path can be one or more analysis magnets 310*a*/310*b* for analyzing the particle beam 304 prior to being directed to the gantry of treatment station 20 at 314. For example, an achromatic dipole set 310*a*/310*b* can perform energy analysis of the particle beam 304.

The beam transport system 18 may also include one or more energy analysis and selection components disposed along the beam path. For example, the fixed energy particle beam 304 from the cyclotron 302 can be decelerated/attenuated by a degrader unit 308, examples of which are known in the art, followed by a set of energy selection dipole magnets dedicated for fine energy selection by filtering undesired traverse emittances, momentum spread and energy spread resulted from the energy degrader unit 308. In some embodiments, the degrader unit 308 can be combined with a momentum spreading unit. In such a configuration, the degrader/momentum spreader combination may be embodied as a single device.

The energy analysis and selection components can include an energy defining slit system 312 at dispersive focus between the dipole set 310*a*/310*b*. At the dispersive focus a high correlation between relative momentum/energy and horizontal distance from the central beam axis can be defined. The slits 312 can be positioned horizontally so as to limit the initially Gaussian shaped momentum/energy distribution behind the energy degrader 308 at dispersive focus, thus allowing for minimum distal fall-off (e.g., 2 mm above the physical limit) of the particles' Bragg-peak and thereby minimizing beam-losses in the subsequent beam transport system. In some embodiments, the slit system 312 may be optionally omitted.

Figure 4:
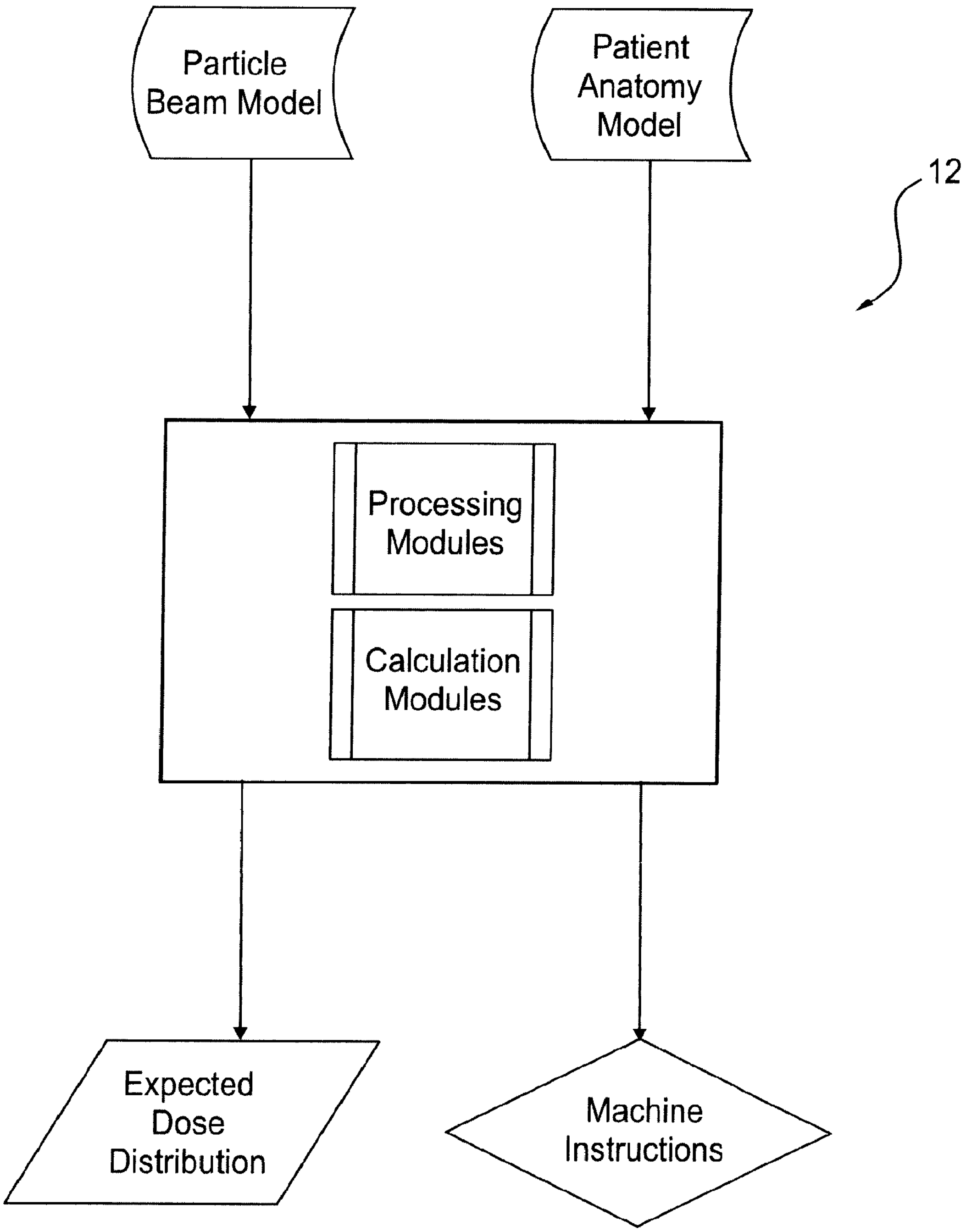
FIG. 4 shows a simplified schematic diagram of various components of a planning treatment device, according to one or more embodiments of the discloses subject matter.

FIG. 4 illustrates a treatment planning module 12, including processes employed by the treatment planning module 12, according to one or more exemplary embodiments. As shown in FIG. 4, the treatment planning module 12 is configured to receive, as input, particle beam and patient anatomy models, apply various processing and calculation processes on the input data, and generate, as outputs, a treatment plan that includes an expected dose distribution within the patient and machine instructions by which different component of the treatment system 100 work together to irradiate the patient so that the actual dose distribution within the patient corresponds to the expected dose distribution.

In the treatment planning module 12, the expected dose distribution D(x, y, z) is determined by employing dose distribution models/algorithms that calculate the delivered dose D at particular locations x, y, z within a medium (i.e., patient) via expressions/formulas that take into consideration the dose at a particular depth z in the medium (i.e., depth dose DD(z) within the medium/patient), as well as the distribution of dose in transversal directions x, y (i.e., transversal dose distributions $T(x, z, \sigma_x(z))$ and $T(y, z, \sigma_y(z))$ within an object/patient). The depth dose DD(z) can be obtained via measurements in a water phantom, via a combination of first principles and data fitting, via analytical approximations, or via Monte Carlo calculations. The transversal dose distributions ($T(x, z, \sigma_x(z)$ and $T(y, z, \sigma_y(z))$ can be calculated starting from measured data about the beam dimension, shape, divergence and direction, and by calculating the beam broadening by modelling the result of relevant physical processes that the particle is exposed while in the medium (i.e., Coulomb scattering and/or nuclear interactions, for example) via weighted components described by a Gaussian distribution. Since some of the properties of the particle beams, for example, the depth z of dose deposition, depend on the initial energy E of the beam, the expected dose distribution model/algorithm also takes into account the energy dependence of the delivered dose.

In order to accurately plan for treatment, the treatment planning module 12 models the depth dose distribution of the particles (e.g., protons, electrons, neutrons, ions, etc.) at different energies that are used for treatment. The depth dose distribution model includes the energy distribution of the particles, specific to the above outlined energy selection process. The model function employed by the treatment planning module 12 determines how accurate the treatment plan will reflect the actual dose distribution in the patient. Moreover, the model function is used to interpolate for intermediate energies of the system, which energies may not have been measured during commissioning of the system. The treatment planning module 12 can take into account, for example, the shape and location of an irradiation volume (e.g., tumor) and a desired irradiation dose, as well as angles and particle energies needed to provide the desired dose. The treatment planning module 12 can then convert the information to instructions for the particle treatment system 100 to produce the particle beam with prescribed energy and/or instruct the magnets to deflect the beam to the desired irradiation volume.

In prior systems, an energy distribution model approximated by a Gaussian has been used. A Gaussian or a Gaussian distribution function (also referred to as a "bell-shaped curve") is a continuous function which approximates a binomial distribution of events, and which represents the probability distribution with a standard deviation σ relative to the average of a random distribution. The Gaussian approximation can be well parametrized over the complete energy range applied in treatment, thereby allowing ready interpolation of the intermediate energies. Such a model can be derived from measurements of depth dose distributions. However, it has been observed that, for lower energies, the energy distribution of the particles is not necessarily Gaussian. Thus, the expected energy distribution in a beam generation system with energy analysis and selection components is not necessarily Gaussian, especially for lower energies. Therefore, using a Gaussian to model energy distribution results in an inaccurate modeling of the dose distribution. An inaccurate dose distribution model results in inaccuracies in the treatment plan. Inaccuracies in the treatment plan can introduce significant errors in target volume irradiation.

Therefore, in one or more embodiments of the disclosed subject matter, the treatment planning module 12 is configured to employ a non-Gaussian model. In particular, in one or more exemplary embodiments, a non-Gaussian model based on a combination of error-functions is generated and used to model the energy distribution. An error function Erf(n) represents the probability that the parameter of interest (i.e., n) is within a range between $$\left(-\frac{n}{\sigma\sqrt{2}}\right) \text{ and } \left(\frac{n}{\sigma\sqrt{2}}\right),$$

where σ represents the started deviation. The model may take the form of:

$$p(E) = a\left(Erf\left(\frac{E+b-c}{d}\right) - Erf\left(\frac{E-b_2-c}{d_2}\right)\right),$$

where p is the distribution of energy E, a is a normalization constant, b and $b_2$ are widths of the profile halves (i.e., full widths at half maximum of the peak of the distribution curve), c is the mean energy, and d and $d_2$ are parameters defining the slope of the spectral higher and lower boundaries (i.e., high and low boundaries of the energy spectrum). In alternative embodiments, a simpler form of the model can have $b_2$ set equal to b and $d_2$ equal to d, yielding a symmetric function of the form:

$$p(E) = a\left(Erf\left(\frac{E+b-c}{d}\right) - Erf\left(\frac{E-b-c}{d}\right)\right).$$

The free parameters of the above models can be determined from measured depth dose distributions by minimizing the quadratic difference to a convolution of the model function with a distribution of a mono-energetic proton or other ion depth dose distribution. The latter might be based on a Monte Carlo calculation or other theoretical models of a Bragg-peak. The optimization process itself can be achieved by employing numerical optimization strategies. In general, the Monte Carlo model follows the propagation of a particle beam in the medium by considering almost all possible interactions of the particle with matter. Each interaction for each particle is considered on the basis of models and/or experimental and evaluated databases for interactions at all levels. Monte Carlo codes are then employed to calculate depth dose, lateral dose profiles, isodose curves and secondary particle production for the particle beams to estimate the dose distribution.

Figure 5:
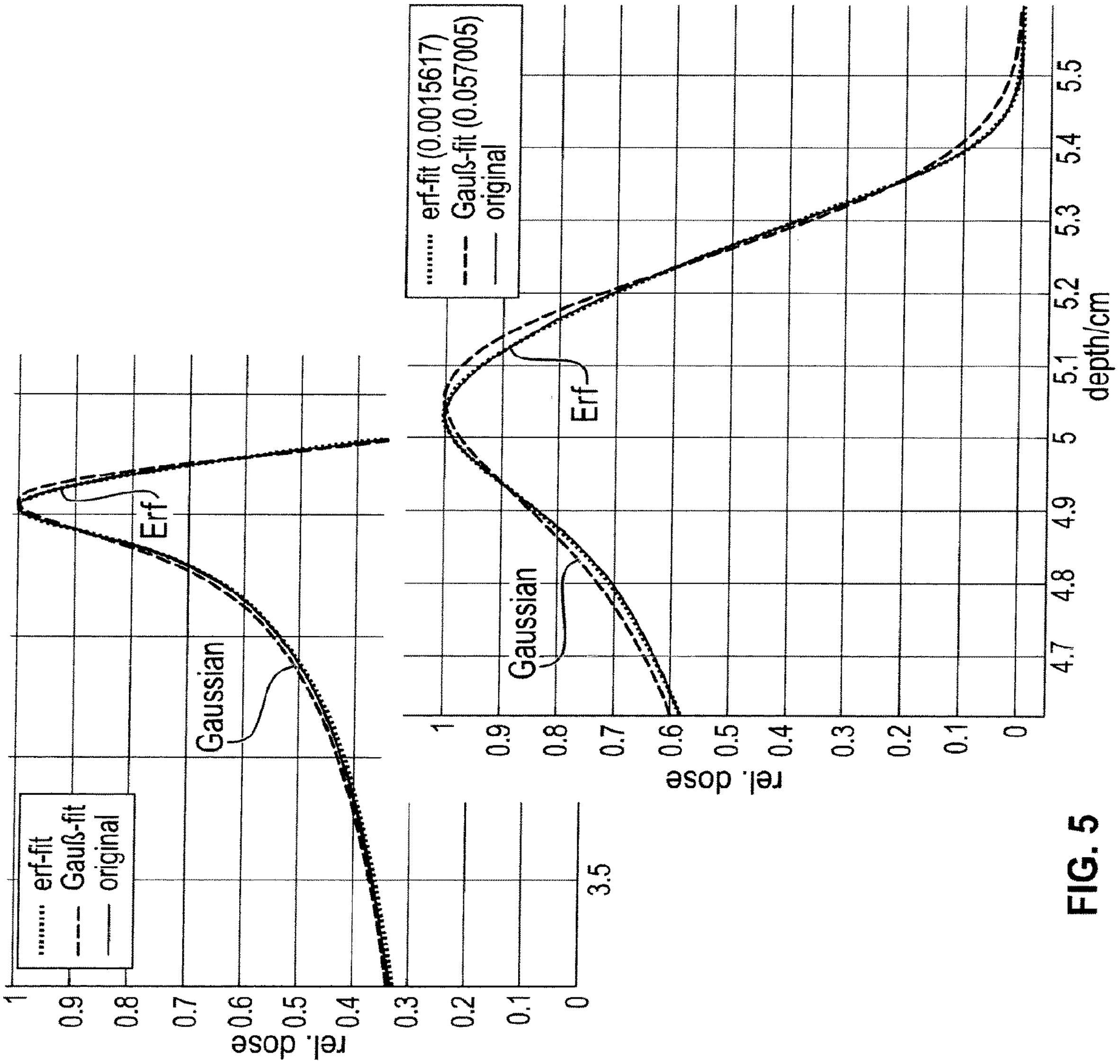
FIG. 5 are graphs of a 80 MeV proton depth dose distribution around the Bragg peak measured (‘original’) in a proton therapy system with a given initial energy spread, which is either approximated as a Gaussian distribution or by an error-function based model, according to one or more embodiments of the disclosed subject matter.
Figure 6A:
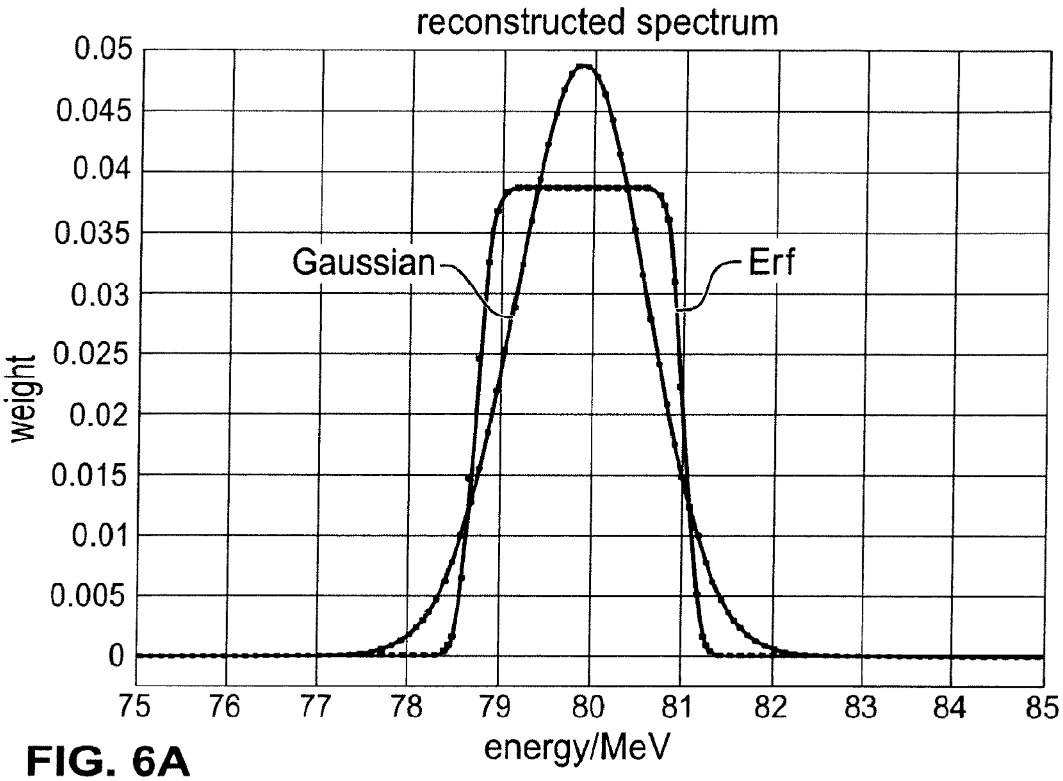
FIGS. 6A-6B are graphs of energy distribution models of FIG. 4, for two different configurations of an energy slit.
Figure 6B:
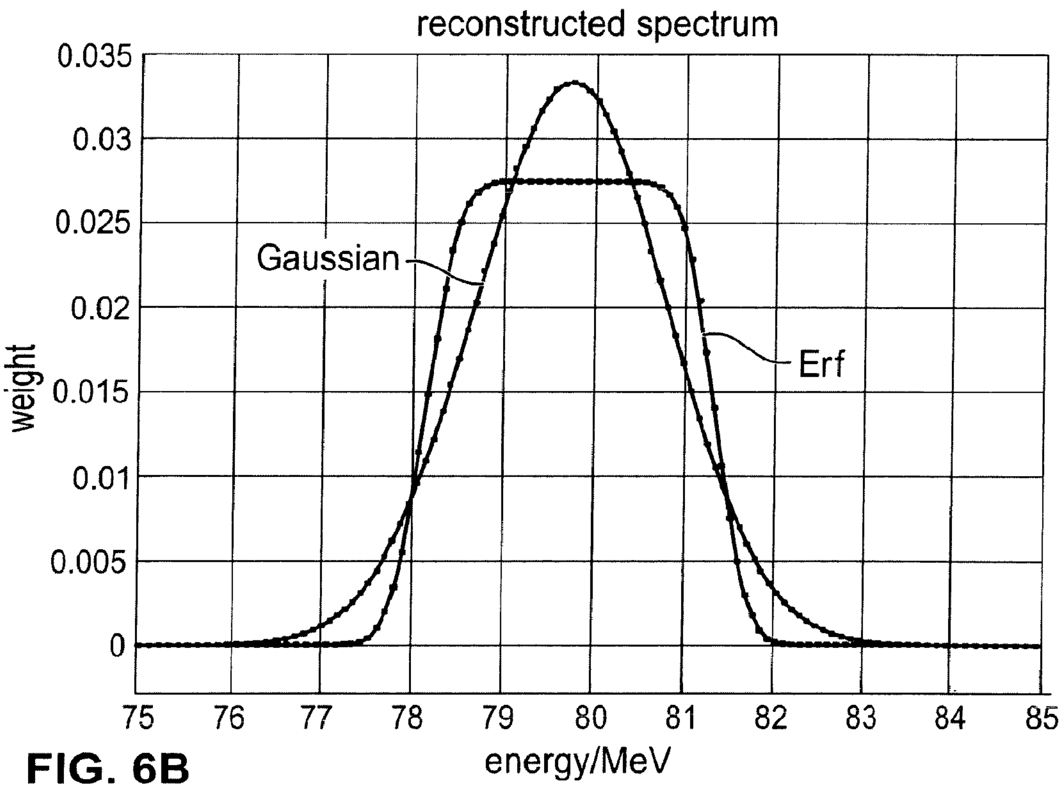
Figure 7:
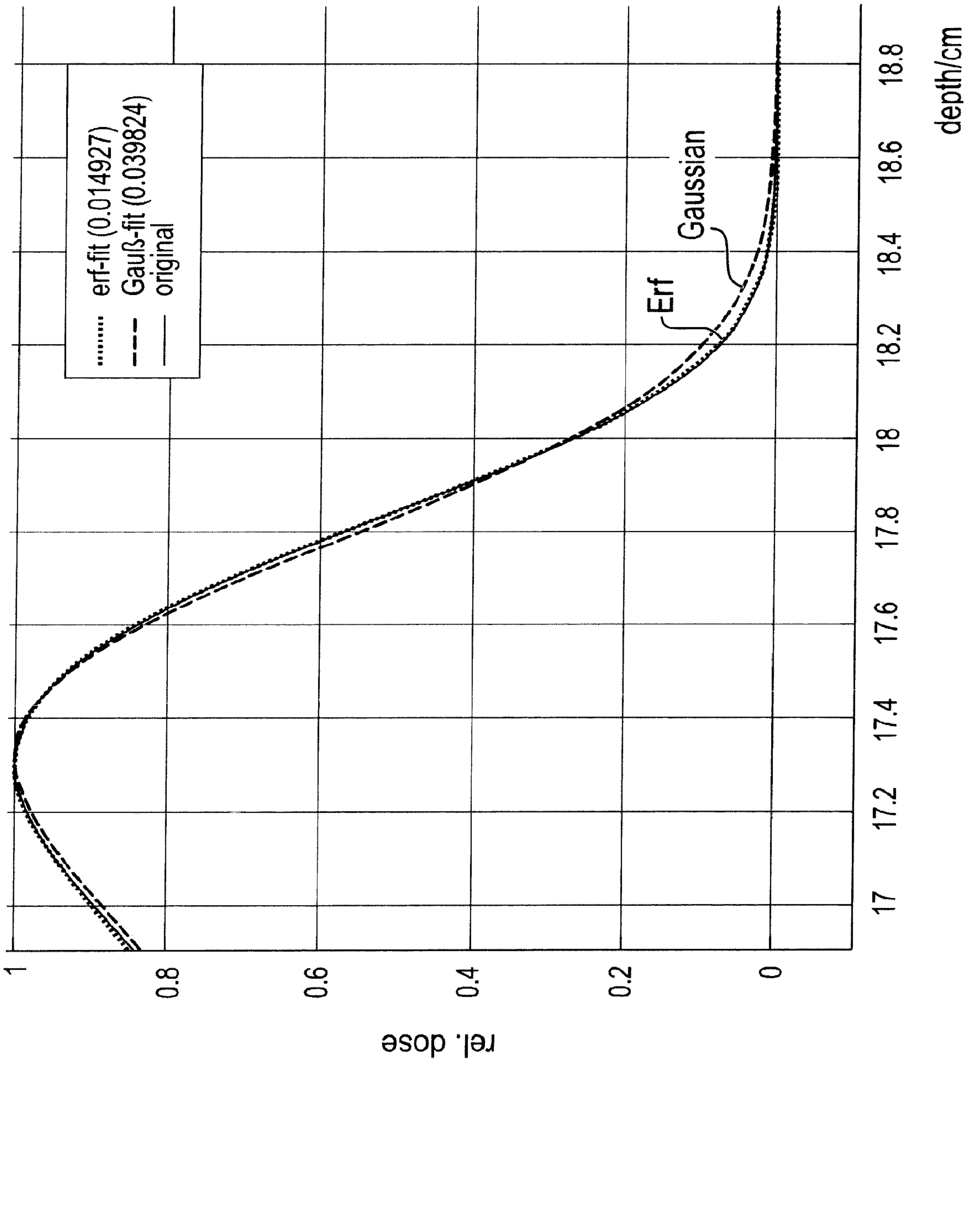
FIG. 7 is a graph of a curve similar to FIG. 5, but showing the Bragg-peak region of the depth dose curve for a 160 MeV proton beam.

In an exemplary embodiment, 80 MeV Bragg-peaks from a proton beam irradiation were measured, Monte Carlo calculations of a 80 MeV mono-energetic beam were made, and convolved with either a Gaussian shaped energy distribution or the non-Gaussian model introduced above. As is evident from FIG. 5, the non-Gaussian model resulted in significantly better fit for 80 MeV beams at two different configurations of the energy analysis and selection system as shown in FIG. 6A and FIG. 6B. Similar improvements can be seen for intermediate energies (e.g., 160 MeV), as shown in FIG. 7. At higher energies, the difference between Gaussian and non-Gaussian decreases. Thus, the non-Gaussian model more closely agrees with actual measurements of the particle beam, especially at low energies, and more closely reflects the expected shape of the actual energy distribution.

Using the above noted non-Gaussian model in the treatment planning module 12 thus better describes the actual energy distribution reaching the patient and thus the resulting depth dose distribution in tissue. The improved representation of the expected particle energy distribution offered by the non-Gaussian model allows for the tailoring of a treatment plan. Indeed, since the biological effectiveness of a particle beam may be dependent on beam energy as well as tissue location and type, the ability to accurately model the energy of the resulting particle beam can allow for the development of a treatment plan that minimizes, or at least reduces, the dose received by the patient while still being effective.

In one or more additional embodiments, the treatment planning module 12 can incorporate additional aspects to the model beyond the above noted non-Gaussian basis. For example, the treatment planning module 12 can perform other forms of deconvolution of the spectrum, including regularization.

Figure 8:
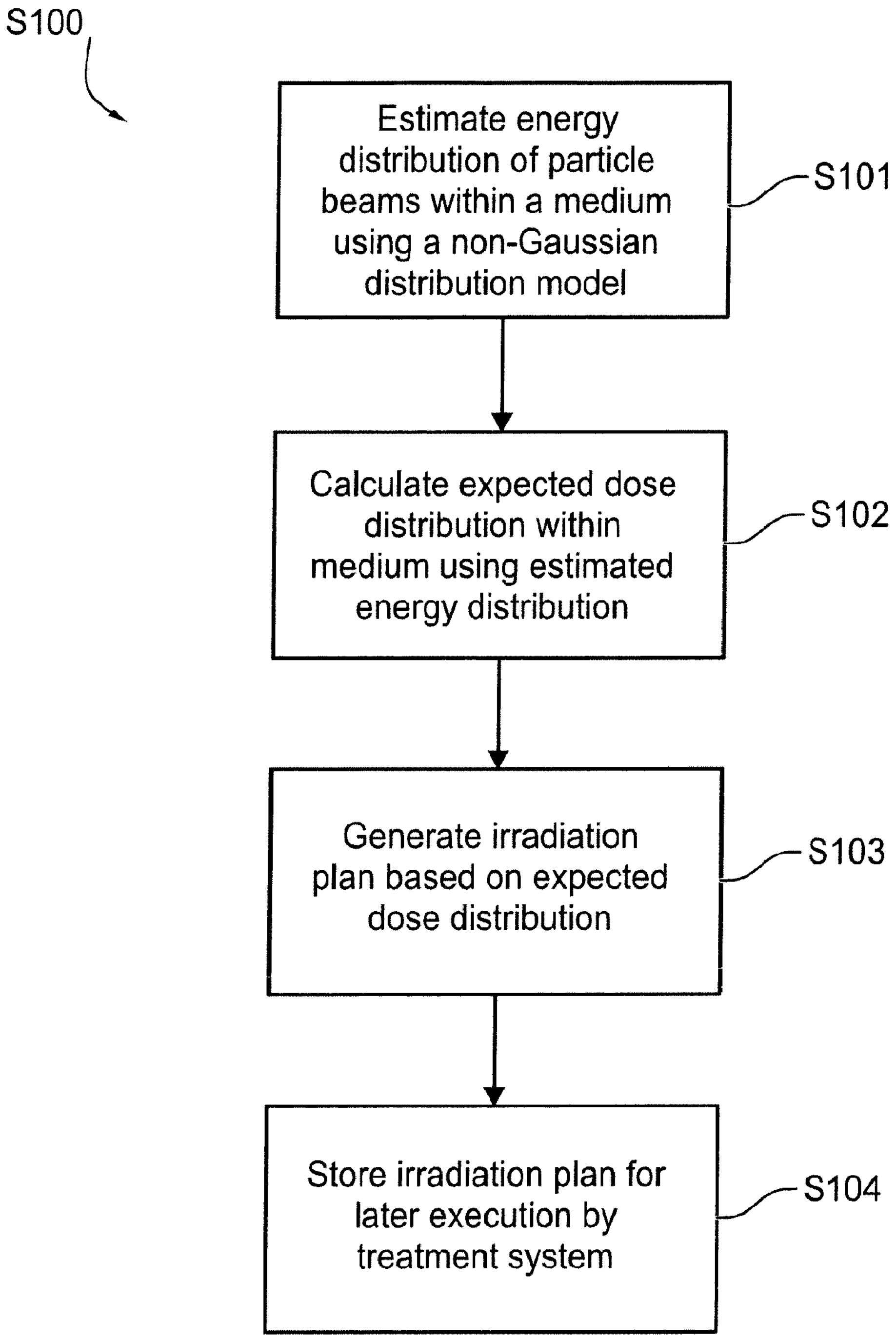
FIG. 8 is an exemplary process for implementing a treatment plan according to different embodiments of the disclosed subject matter.

In one or more additional embodiments, a process S100 can be implemented by the particle therapy system 10, as shown in FIG. 8, including/comprising the following steps: in step S101, the treatment planning module 12 estimates the energy distribution of the particle beams within a medium using a non-Gaussian distribution model. In exemplary embodiments, the medium could be a phantom approximating/simulating a body part of a patient to be treated at the treatment station 20. The non-Gaussian distribution model can be based on a combination of error-functions generated and used to model the energy distribution. For example, the model may take the form of:

$$p(E) = a\left(Erf\left(\frac{E+b-c}{d}\right) - Erf\left(\frac{E-b_2-c}{d_2}\right)\right),$$

where p is the distribution of energy E, a is a normalization constant, b and $b_2$ are widths of the profile halves (i.e., full widths at half maximum of the peak of the distribution curve), c is the mean energy, and d and $d_2$ are parameters defining the slope of the spectral higher and lower boundaries (i.e., high and low boundaries of the energy spectrum). In alternative embodiments, a simpler form of the model can have $b_2$ set equal to b and $d_2$ equal to d, yielding a symmetric function of the form:

$$p(E) = a\left(Erf\left(\frac{E+b-c}{d}\right) - Erf\left(\frac{E-b-c}{d}\right)\right).$$

In Step S102, the treatment planning module 12 calculates the expected dose distribution within the medium using the estimated energy distribution applied in step S101. Based on the calculated expected dose distribution, in step S103, the treatment planning module 12 generates a treatment plan, and in S104, stores the treatment plan in an internal and/or external storage medium, to be later retrieved and executed by the treatment system 10 during irradiation of the patient with particle beams in treatment station 20.

Additional steps may be included in the process, such as, a quality measurement step, wherein the execution of the treatment plan is verified to make sure that the actual dose in the patient corresponds with the calculated expected dose, as well as a quality control step, wherein, if a discrepancy is detected between the expected and the actual dose, the radiation treatment is stopped or a control signal is generated to either automatically halt the treatment or to allow the appropriate medical personnel to manually stop the treatment and/or to determine and correct/remedy the cause of the discrepancy.

Although descriptions above may specifically relate to proton beam system, embodiments of the disclosed subject matter are not limited thereto. Unless specifically disclosed as such, the descriptions above apply to various types of particle therapy systems, including those generating charged particle beams and ion beams, not just proton beams.

It will be appreciated that the aspects of the disclosed subject matter can be implemented, fully or partially, in hardware, hardware programmed by software, software instruction stored on a computer readable medium (e.g., a non-transitory computer readable medium), or any combination of the above.

For example, components of the disclosed subject matter, including components such as a controller, process, or any other feature, can include, but are not limited to, a personal computer or workstation or other such computing system that includes a processor, microprocessor, microcontroller device, or is comprised of control logic including integrated circuits such as, for example, an application specific integrated circuit (ASIC).

Features discussed herein can be performed on a single or distributed processor (single and/or multi-core), by components distributed across multiple computers or systems, or by components co-located in a single processor or system. For example, aspects of the disclosed subject matter can be implemented via a programmed general purpose computer, an integrated circuit device, (e.g., ASIC), a digital signal processor (DSP), an electronic device programmed with microcode (e.g., a microprocessor or microcontroller), a hard-wired electronic or logic circuit, a programmable logic circuit (e.g., programmable logic device (PLD), programmable logic array (PLA), field-programmable gate array (FPGA), programmable array logic (PAL)), software stored on a computer-readable medium or signal, an optical computing device, a networked system of electronic and/or optical devices, a special purpose computing device, a semiconductor chip, a software module or object stored on a computer-readable medium or signal.

When implemented in software, functions may be stored on or transmitted over as one or more instructions or code on a computer-readable medium. The steps of a method or algorithm disclosed herein may be embodied in a processor-executable software module, which may reside on a computer-readable medium. Instructions can be compiled from source code instructions provided in accordance with a programming language. The sequence of programmed instructions and data associated therewith can be stored in a computer-readable medium (e.g., a non-transitory computer readable medium), such as a computer memory or storage device, which can be any suitable memory apparatus, such as, but not limited to read-only memory (ROM), programmable read-only memory (PROM), electrically erasable programmable read-only memory (EEPROM), random-access memory (RAM), flash memory, disk drive, etc.

As used herein, computer-readable media includes both computer storage media and communication media, including any medium that facilitates transfer of a computer program from one place to another. Thus, a storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer.

Also, any connection is properly termed a computer-readable medium. For example, if the software is transmitted from a website, server, or other remote source using a transmission medium (e.g., coaxial cable, fiber optic cable, twisted pair, digital subscriber line (DSL), or wireless technologies such as infrared, radio, and microwave), then the transmission medium is included in the definition of computer-readable medium. Moreover, the operations of a method or algorithm may reside as one of (or any combination of) or a set of codes and/or instructions on a machine readable medium and/or computer-readable medium, which may be incorporated into a computer program product.

One of ordinary skill in the art will readily appreciate that the above description is not exhaustive, and that aspects of the disclosed subject matter may be implemented other than as specifically disclosed above. Indeed, embodiments of the disclosed subject matter can be implemented in hardware and/or software using any known or later developed systems, structures, devices, and/or software by those of ordinary skill in the applicable art from the functional description provided herein.

In this application, unless specifically stated otherwise, the use of the singular includes the plural, and the separate use of "or" and "and" includes the other, i.e., "and/or." Furthermore, use of the terms "including" or "having," as well as other forms such as "includes," "included," "has," or "had," are intended to have the same effect as "comprising" and thus should not be understood as limiting.

Any range described herein will be understood to include the endpoints and all values between the endpoints. Whenever "substantially," "approximately," "essentially," "near," or similar language is used in combination with a specific value, variations up to and including 10% of that value are intended, unless explicitly stated otherwise. The foregoing descriptions apply, in some cases, to examples generated in a laboratory, but these examples can be extended to production techniques. Thus, where quantities and techniques apply to the laboratory examples, they should not be understood as limiting. In particular, where specific chemicals or materials have been disclosed herein, other chemicals and materials may also be employed according to one or more contemplated embodiments.

It is thus apparent that there is provided in accordance with the present disclosure, spectrum modeling systems, methods, and devices for particle therapy treatment planning. Many alternatives, modifications, and variations are enabled by the present disclosure.

While specific examples have been shown and described in detail to illustrate the application of the principles of the present invention, it will be understood that the invention may be embodied otherwise without departing from such principles. For example, disclosed features may be combined, rearranged, omitted, etc. to produce additional embodiments, while certain disclosed features may sometimes be used to advantage without a corresponding use of other features. Accordingly, Applicant intends to embrace all such alternative, modifications, equivalents, and variations that are within the spirit and scope of the present invention.

The invention claimed is:

1. A method for generating a treatment plan, the method comprising executing by a computer processor the following steps:

applying a non-Gaussian model comprising a combination of error functions to estimate depth dose distribution and energy distribution of particles within a medium; optimizing the non-Gaussian model based on propagation of the particles within the medium and interactions of the particles with the medium;

determining a dose distribution for one or more particle beams, or portions thereof, from a particle therapy system, based on the estimated depth dose distribution;

generating a treatment plan based on the determined dose distribution, the treatment plan including an irradiation plan and additional information, the additional information including desired radiation dose within the medium, and angles and particle energies needed to provide the desired radiation dose; and generating machine instructions for the particle therapy system to effect the irradiation plan based on the additional information, wherein the non-Gaussian model is given by:

$$p(E) = a\left(Erf\left(\frac{E+b-c}{d}\right) - Erf\left(\frac{E-b-c}{d}\right)\right),$$

or $$p(E) = a\left(Erf\left(\frac{E+b-c}{d}\right) - Erf\left(\frac{E-b_2-c}{d_2}\right)\right),$$

where p is the distribution of energy E, a is a normalization constant, b and $b_2$ are widths of a profile half, c is a mean energy, and d and d, are parameters defining a slope of spectral higher and lower boundaries.

2. The method of claim 1, further comprising, irradiating a patient with the one or more particle beams, or portions thereof, based at least in part on the determined dose distribution.

3. The method of claim 2, further comprising calculating a radiation dose from the one or more particle beams, or portions thereof, within the patient based on the energy distribution.

4. The method of claim 3, wherein the calculating of the radiation dose employs an analytical function or a stochastic algorithm.

5. The method of claim 2, wherein the irradiating includes adjusting an energy of the one or more particle beams, or portions thereof, from a particle accelerator using at least one of a degrader and an energy defining slit.

6. The method of claim 1, wherein the one or more particle beams comprise protons, ions, or other charged particles.

7. A non-transitory computer readable medium upon which is embodied a sequence of programmed instructions, which when executed by a computer processing system, causes the computer processing system to:

apply a non-Gaussian model comprising a combination of error functions to estimate depth dose distribution and energy distribution of particles within a medium; optimize the non-Gaussian model based on propagation of the particles within the medium and interactions of the particles with the medium;

determine a dose distribution for one or more particle beams, or portions thereof, from a particle therapy system, based on the estimated depth dose distribution;

generate a treatment plan based on the determined dose distribution, the treatment plan including an irradiation plan and additional information, the additional information including desired radiation dose within the medium, and angles and particle energies needed to provide the desired radiation dose; and generate machine instructions for the particle therapy system to effect the irradiation plan based on the additional information, wherein the non-Gaussian model is given by:

$$p(E) = a\left(Erf\left(\frac{E+b-c}{d}\right) - Erf\left(\frac{E-b-c}{d}\right)\right),$$

or $$p(E) = a\left(Erf\left(\frac{E+b-c}{d}\right) - Erf\left(\frac{E-b_2-c}{d_2}\right)\right),$$

where p is the distribution of energy E, a is a normalization constant, b and $b_2$ are widths of a profile half, c is a mean energy, and d and $d_2$ are parameters defining a slope of spectral higher and lower boundaries.

8. The non-transitory computer readable medium of claim 7, wherein the determining of the dose distribution further employs an analytical function or a stochastic algorithm.

* * * * *